United States Patent
Fan et al.

(10) Patent No.: US 9,200,999 B2
(45) Date of Patent: Dec. 1, 2015

(54) METHOD AND SYSTEM FOR CHARACTERIZING COLOR VARIATION OF A SURFACE

(71) Applicant: GM GLOBAL TECHNOLOGY OPERATIONS LLC, Detroit, MI (US)

(72) Inventors: Hua-Tzu Fan, Troy, MI (US); Samuel Lute, Orion, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 79 days.

(21) Appl. No.: 14/023,539

(22) Filed: Sep. 11, 2013

(65) Prior Publication Data

US 2015/0070694 A1    Mar. 12, 2015

(51) Int. Cl.
| | |
|---|---|
| *G01J 3/46* | (2006.01) |
| *G01N 21/25* | (2006.01) |
| *G01J 3/40* | (2006.01) |
| *G01J 3/50* | (2006.01) |

(52) U.S. Cl.
CPC .................. *G01N 21/255* (2013.01); *G01J 3/40* (2013.01); *G01J 3/50* (2013.01); *G01J 3/504* (2013.01); *G01J 2003/467* (2013.01)

(58) Field of Classification Search
CPC ............... G01J 3/40; G01J 3/50; G01J 3/504; G01J 2003/466; G01J 2003/467
USPC .................................................. 356/402, 319
See application file for complete search history.

(56) References Cited

U.S. PATENT DOCUMENTS

| | | | | |
|---|---|---|---|---|
| 3,690,771 | A * | 9/1972 | Armstrong et al. | 356/405 |
| 5,590,251 | A * | 12/1996 | Takagi | 345/604 |
| 5,929,998 | A * | 7/1999 | Kettler et al. | 356/405 |
| 2004/0190768 | A1* | 9/2004 | Nonogaki et al. | 382/162 |
| 2007/0104663 | A1* | 5/2007 | Henglein et al. | 424/61 |
| 2009/0213120 | A1* | 8/2009 | Nisper et al. | 345/426 |
| 2014/0242271 | A1* | 8/2014 | Prakash et al. | 427/140 |

* cited by examiner

*Primary Examiner* — Kara E Geisel
*Assistant Examiner* — Dominic J Bologna
(74) *Attorney, Agent, or Firm* — Quinn Law Group, PLLC

(57) ABSTRACT

A system and method of characterizing a color variation of a surface includes a device having a light source and a plurality of sensors positioned at respective viewing angles. An algorithm is stored on and executable by a controller to cause the controller to direct a beam of light at the measurement location with the light source and measure the light leaving the measurement location with the sensors at a plurality of azimuth angles to obtain respective measured color values. The controller is configured to define a color vector function $F(\theta, \phi)$ to represent the color variation of the surface. The controller is configured to determine the color vector function $F(\theta, \phi)$ based at least partially on the respective measured color values. The system allows for a representation of color space of a surface at any azimuth and viewing angle.

17 Claims, 2 Drawing Sheets

METHOD AND SYSTEM FOR CHARACTERIZING COLOR VARIATION OF A SURFACE

TECHNICAL FIELD

The disclosure relates generally to a method and system for characterizing the color variation of a surface.

BACKGROUND

The coating of automobile bodies may include metallic and other types of special-effect paints containing various pigments. Such paints may contain a coating of lustrous particles such as aluminum flakes, mica flakes and xirallic that act as tiny mirrors. When the paint is illuminated from a single direction, light is reflected from the surfaces of these particles. The directional reflectance of metallic and other types of special-effect paints results in a variation in color of the surface based on the angle of observation of the viewer and other factors.

SUMMARY

A system and method of characterizing a color variation of a surface includes a device having a light source configured to direct a beam of light on a measurement location on the surface. The system may be used to represent or model color space at any azimuth and viewing angle, for example, the surface of a vehicle having angular variations due to non-uniform distribution of flake orientations in paint film. In one example, the system is used on a prototype coated surface to determine the esthetic appeal of the prototype coated surface to a viewer, based on variations in color of the surface at different angles of observation. An accurate representation of the color variation of a prototype coated surface enhances decision making between different metallic/special-effect paint selections. In addition, this mathematical representation of colors enable digitalization of colors so that computer graphic and rendering software can represent and reproduce colors more accurately in displays or prints.

The device is rotatable to a plurality of azimuth angles ($\theta_1$, $\theta_2 \ldots \theta_e$), relative to the measurement location. The total number of the plurality of azimuth angles is at least a first number (e). The device includes a plurality of sensors positioned at respective viewing angles ($\phi_1$, $\phi_2 \ldots \phi_g$). The total number of the respective viewing angles is at least a second number (g).

A controller is operatively connected to the device. An algorithm is stored on and executable by the controller to cause the controller to direct a beam of light at the measurement location with the light source being at an illumination angle $\alpha$ relative to the measurement location. The controller is further configured to measure the light leaving the measurement location with the plurality of sensors at each of the plurality of azimuth angles ($\theta_1$, $\theta_2 \ldots \theta_e$) to obtain respective measured color values.

The controller is configured to define a color vector function $F(\theta, \phi)$ as a product of a first vector $P(\theta)$ and a second vector $Q(\phi)$ such that $F(\theta, \phi)=P(\theta).Q(\phi)$. The color vector function $F(\theta, \phi)$ represents the color variation of the surface. The controller is configured to determine the color vector function $F(\theta, \phi)$ based at least partially on the respective measured color values.

The color vector function $F(\theta, \phi)$ and first and second vectors $P(\theta)$, $Q(\phi)$ each include respective first, second and third components, such that $F(\theta, \phi)=[F_1(\theta, \phi), F_2(\theta, \phi), F_3(\theta, \phi)]$, $P(\theta)=[P_1(\theta), P_2(\theta), P_3(\theta)]$ and $Q(\phi)=[Q_1(\phi), Q_2(\phi), Q_3(\phi)]$. The respective first component of the color vector function $F(\theta, \phi)$ may represent one of a lightness component (L*), a redness/greenness component (a*), and a yellowness/blueness component (b*).

Determining the color vector function $F(\theta, \phi)$ based at least partially on the respective measured color values includes expressing the first components $P_1(\theta)$, $Q_1(\phi)$ as a product of respective plurality of matrices and obtaining respective first and second set of coefficients by inputting the measured color values into the respective plurality of matrices. The first component $F_1(\theta, \phi)$ of the color vector function $F(\theta, \phi)$ is obtained based on the first and second set of coefficients.

Defining the color vector function $F(\theta, \phi)$ includes expressing the respective first component $P_1(\theta)$ as: $P_1(\theta) = a_0/2 + \sum_{j=1 \text{ to } f} [a_j \cos(j\theta) + b_j \sin(j\theta)]$; wherein $a_0$, $a_j$, $b_j$ are a first set of coefficients and $b_{j=f}$ is zero if the first number (e) is even. The integer parameter f is defined such that $f=e/2$ and $f=(e-1)/2$ if the first number (e) is even and odd, respectively.

Defining the color vector function $F(\theta, \phi)$ includes expressing the respective first component $Q_1(\phi)$ as: $Q_1(\phi) = c_0/2 + \sum_{k=1 \text{ to } h} [c_k \cos(k\phi) + d_k \sin(k\phi)]$; wherein $c_0$, $c_k$, $d_k$ are a second set of coefficients and $d_{k=h}$ is zero if the second number (g) is even. The integer parameter h is defined such that $h=g/2$ and $h=(g-1)/2$ if the second number (g) is even and odd, respectively.

The plurality of azimuth angles ($\theta_1$, $\theta_2 \ldots \theta_e$) may be evenly-spaced. In one example, the illumination angle is approximately 45 degrees.

The above features and advantages and other features and advantages of the present invention are readily apparent from the following detailed description of the best modes for carrying out the invention when taken in connection with the accompanying drawings.

DETAILED DESCRIPTION

Figures 1, 2:
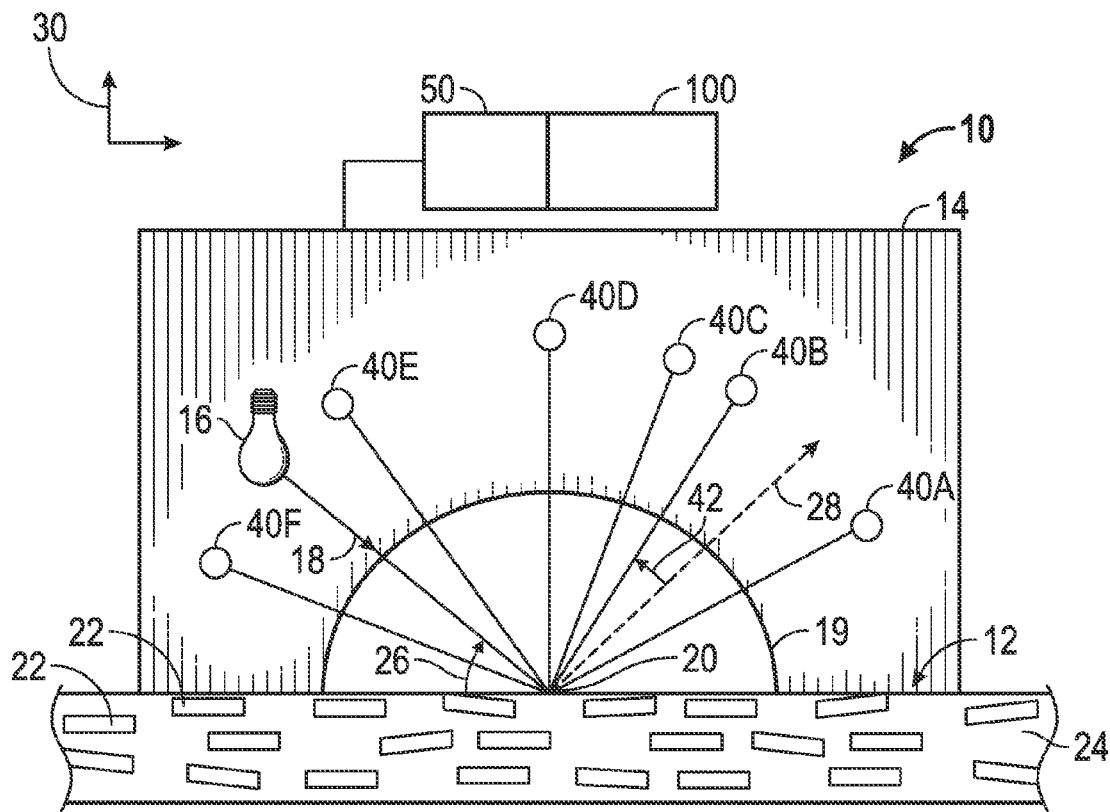
FIG. 1 is a schematic diagram of a system for characterizing a color variation of a surface.
FIG. 2 is a three-dimensional schematic diagram of the system of FIG. 1.

Referring to the Figures, wherein like reference numbers refer to the same or similar components throughout the several views, FIG. 1 is a schematic diagram of a system 10 for characterizing a color variation of a surface 12. The system 10 includes a device 14 (lightly shaded) having a light source 16 configured to direct a beam of light 18 on a measurement location 20 on the surface 12. The device 14 may include a window 19 that allows light to pass through. The light source 16 may emit electromagnetic radiation covering the visible spectrum, also known as white light. Alternatively, the light source 16 may emit broadband radiation, covering the visible and non-visible spectrum.

Referring to FIG. 1, the surface 12 is a painted surface having a plurality of metallic particles 22 embedded in the paint film 24. The surface 12 may be an exterior surface of an automobile that is coated with a metallic or other special-effect paint. The metallic particles 22 include, but are not limited to, aluminum flakes, mica flakes and xirallic that act as tiny mirrors. The metallic particles 22 may be non-uniformly distributed under the surface 12. The system 10 described herein may be used to represent or model color variation on an exterior surface of an automobile or other painted surfaces due to non-uniform distribution of the metallic particles 22.

The measurement plane of FIG. 1 (i.e., the plane of the page) is indicated at numeral 30 in FIG. 1. FIG. 2 is a three-dimensional schematic diagram of the system 10. For clarity, some components of FIG. 1 are not shown in FIG. 2. Measurement plane 30 of FIG. 1 is indicated in FIG. 2 and lightly shaded. Referring to FIGS. 1-2, the light source 16 is positioned at an illumination angle 26 relative to the measurement location 20. Any value for the illumination angle 26 may be chosen. In one example, the illumination angle 26 is approximately 45 degrees. Referring to FIG. 1, when the beam of light 18 illuminates the surface 12 from a single direction, light is reflected from the surfaces of the metallic particles 22. Referring to FIGS. 1-2, the reflected light also includes a specular component indicated at specular line 28, which is a mirror-like reflection such that the angle of incidence equals the angle of reflection, as well as a diffuse light component (not shown).

Referring to FIG. 2, the device 14 may be rotated to an azimuth angle 32 ($\theta$). The azimuth angle 32 ($\theta$) is formed between a reference direction 34 (the x-axis in FIG. 2) and a line 36 extending from the measurement location 20 to a point of interest 38 projected from the measurement plane 30 to the same plane as the reference direction 34. The device 14 is configured to be rotatable to a plurality of azimuth angles 32 ($\theta_1, \theta_2 \ldots \theta_e$), relative to the measurement location 20. The total number of the azimuth angles 32 is at least a first number (e). In one example, the azimuthal angles 32 are 0°, 90°, 180°, and 270° (such that e=4). The azimuth angles 32 ($\theta_1, \theta_2 \ldots \theta_e$) may be evenly-spaced.

Referring to FIG. 1, the device 14 includes a plurality of sensors 40A-F positioned at respective viewing angles 42 ($\phi_1, \phi_2 \ldots \phi_g$). Referring to FIGS. 1-2, the viewing angles 42 ($\phi$) are measured from the specular line 28. For clarity, only sensor 40B is indicated in FIG. 2. It is to be appreciated that any number of sensors positioned at any angle may be employed. As shown in FIG. 1, the sensors 40A-F and light source 16 are positioned in the same measurement plane 30. The total number of the respective viewing angles is at least a second number (g). In the non-limiting example shown in FIG. 1, the respective viewing angles 42 for sensors 40A-F are −15°, 15°, 25°, 45°, 75°, and 110°, respectively (such that g=6).

Figure 3:
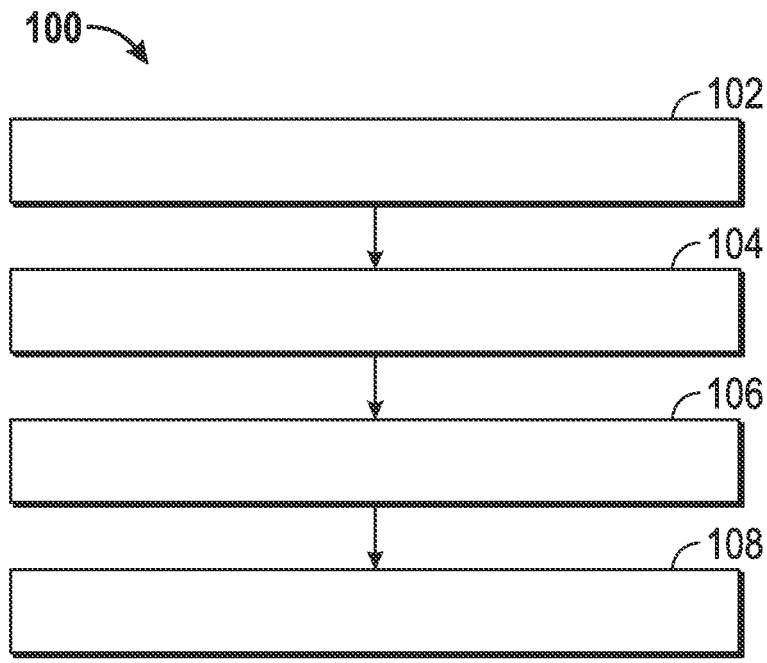
FIG. 3 is an example flow chart for a method or algorithm for characterizing the color variation of the surface shown in FIG. 1.

Referring to FIG. 1, a controller 50 is operatively connected to the device 14. Controller 50 executes a method or algorithm 100 which is stored on or is otherwise readily executable by the controller 50. FIG. 3 is a flow chart showing the method 100. The controller 50 is adapted to characterize a color variation of the surface 12. The controller 50 may be a general-purpose digital computer, a microprocessor, central processing unit, or a computer-readable storage medium.

The device 14 may be a spectrophotometer that physically measures color values which are outputted to the controller 50. A spectrophotometer such as the Byk-mac (manufactured by BYK-Gardner USA) may be employed for the device 14. The device 14 may be configured to measure color values in L*a*b* (CIELAB 1978) color space, specified by the International Commission on Illumination. However, any other color space system known to those skilled in the art may be employed.

Each of the respective measured color values (measured by the device 14 of FIG. 1) may include a lightness component (L*), a redness/greenness component (a*) and yellowness/blueness component (b*). The lightness component (L*) represents the lightness of the measurement, for example, L*=0 may indicate black and L*=100 may indicate diffuse white. The redness/greenness component (a*) indicates position between red/magenta and green, for example, negative values of a* may indicate green while positive values indicate red/magenta. The yellowness/blueness component (b*) indicates position between yellow and blue, for example, negative values of b* may indicate blue while positive values may indicate yellow.

Referring to FIG. 3, the algorithm 100 may begin at step 102 in which the controller 50 is configured to (i.e., the algorithm 100 causes the controller 50 to) direct a beam of light 18 through the light source 16 at the measurement location 20 (see FIG. 1). The steps may be carried out in an order other than that indicated below and one or more steps may be omitted.

In step 104 of FIG. 3, the controller 50 is configured to measure the light leaving the measurement location 20 with the plurality of sensors 40A-F at each of the plurality of azimuth angles 32 ($\theta_1, \theta_2 \ldots \theta_e$) to obtain respective measured color values. As previously noted, any number of sensors and azimuth angles 32 may be employed.

In step 106 of FIG. 3, the controller 50 is configured to define a color vector function F($\theta, \phi$) as a product of a first vector P($\theta$) dependent on the azimuth angles 32 ($\theta$) and a second vector Q($\phi$) dependent on the respective viewing angles 42 ($\phi$) such that F($\theta, \phi$)=P($\theta$).Q($\phi$). The color vector function F($\theta, \phi$) represents the color variation of the surface 12.

The color vector function F($\theta, \phi$) and first and second vectors P($\theta$), Q($\phi$) each include respective first, second and third components, such that F($\theta, \phi$)=[$F_1(\theta, \phi), F_2(\theta, \phi), F_3(\theta, \phi)$], P($\theta$)=[$P_1(\theta), P_2(\theta), P_3(\theta)$] and Q($\phi$)=[$Q_1(\phi), Q_2(\phi), Q_3(\phi)$]. The respective first components $F_1(\theta, \phi), P_1(\theta)$ and $Q_1(\phi)$ may represent the lightness value (L*) or redness/greenness value (a*) or yellowness/blueness value (b*). All the respective first components $F_1(\theta, \phi), P_1(\theta)$ and $Q_1(\phi)$ represent the same color space value. Steps 106 and 108 (indicated below) may be applied to each of the first, second and third components of the color vector function F($\theta, \phi$) in turn.

Defining the color vector function F($\theta, \phi$) in step 106 includes representing the first component $P_1(\theta)$ of the first vector P($\theta$) as a first function dependent on the azimuth angle 32 ($\theta$) (see FIG. 1) and a first set of coefficients. In one example, the first function is represented as:

$$P_1(\theta) = a_0/2 + \sum_{j=1 \, to \, f} [a_j \cos(j\theta) + b_j \sin(j\theta)] \qquad \text{eq. (1)}$$

If the first number (e) is even, an integer parameter f is defined such that f=e/2. If e is odd, f=(e−1)/2. The first set of coefficients in this case includes $a_0, a_j, b_j$, where j=1 to f. The coefficient $b_{j=f}$ is set as zero if the first number (e) is even.

Defining the color vector function F($\theta, \phi$) in step 106 includes representing the first component $Q_1(\phi)$ of the second vector as a second function dependent on the viewing angle 42 ($\phi$) (see FIGS. 1-2) and a second set of coefficients. In one example, the second function is represented as:

$$Q_1(\phi) = c_0/2 + \sum_{k=1 \, to \, h} [c_k \cos(k\phi) + d_k \sin(k\phi)] \qquad \text{eq. (2)}$$

If the second number (g) is even, an integer parameter h is defined such that h=g/2. If g is odd, h=(g−1)/2. The second set of coefficients in this case includes $c_0, c_k, d_k$, where k=1 to h. The coefficient $d_{k=h}$ is set as zero if the second number (g) is even.

In step 108 of FIG. 3, the controller 50 is configured to determine the color vector function F(θ, φ) based at least partially on the respective measured color values. Step 108 may be completed through a plurality of steps 110, 112 and 114, shown in FIG. 4.

Figure 4:
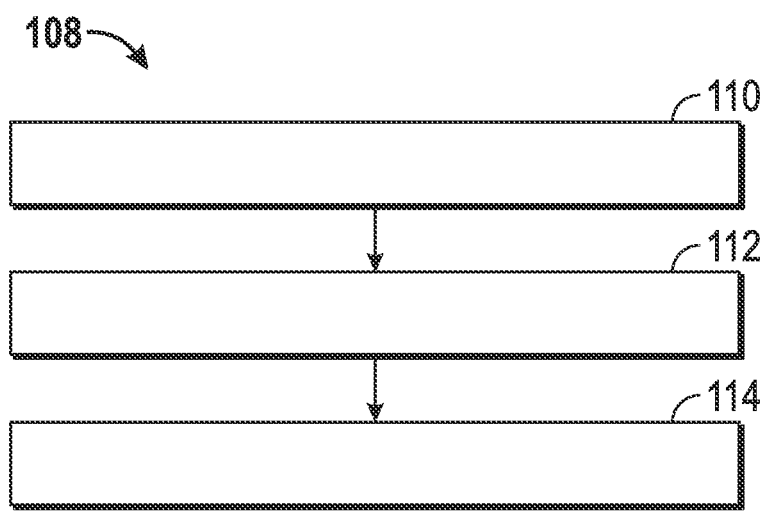
FIG. 4 is a flow chart for a portion of the method or algorithm of FIG. 3.

At step 110 of FIG. 4, if the respective viewing angles 42 (φ) (see FIG. 1) are not equally spaced, the controller 50 may be configured to convert the measured color values into corresponding respective equally-spaced color values. For t non-equally spaced measuring data points, $(\phi_0, Q_0)$, $(\phi_1, Q_1), \ldots, (\phi_k, Q_k), \ldots, (\phi_{t-1}, Q_{t-1})$, the corresponding equally-spaced measuring data points are $(\phi'_0, Q'_0)$, $(\phi'_1, Q'_1), \ldots, (\phi'_k, Q'_k), \ldots, (\phi'_{t-1}, Q'_{t-1})$ with the following relationship:

$\phi'_0=\phi_0$, $Q'_0=Q_0$, $\phi'_{t-1}=\phi_{t-1}$, and $Q'_{t-1}=Q_{t-1}$. For k=1 to t−1, $Q'_k$ is determined by:

$$[(\phi'_k-\phi'_{k-1})(Q_k-Q_{k-1})/(\phi_k-\phi_{k-1})]+Q_{k-1} \qquad \text{eq. (3)}$$

where $[(\phi'_k=\phi'_0+k/t\phi'_{t-1}-\phi'_0)]$     eq. (4)

At step 112 of FIG. 4, controller 50 is configured to express the respective first components $P_1(\theta)$, $Q_1(\phi)$ of the first and second vectors $P(\theta)$, $Q(\phi)$ as a product of respective plurality of matrices. Setting $P_1(\theta)=A\,p$ and $Q_1(\theta)=q^T B^T$, leads to:

$$F_1(\theta,\phi)=P_1(\theta)Q_1(\phi)=Apq^TB^T \qquad \text{eq. (5)}$$

As known to those skilled in the art, the transpose of a matrix B is another matrix $B^T$ where the rows of B are the columns of $B^T$ and the columns of B are the rows of $B^T$. The unknowns in Eq. (5) are $pq^T$, a matrix comprising the first and second set of coefficients (such as in Equations 1-2). Solving this matrix equation by double matrix inversion leads to:

$$A^{-1}Apq^TB^TB^{-T}=A^{-1}F_1B^{-T} \qquad \text{eq. (6)}$$

$$pq^T=A^{-1}F_1B^{-T} \qquad \text{eq. (7)}$$

Here $F_1$ is a matrix with elements comprising the respective measured color values.

At step 114 of FIG. 4, controller 50 is configured to input the measured color values (matrix $F_1$) into the respective plurality of matrices to obtain the first and second set of coefficients. In the example outlined above, the first and second set of coefficients are $a_0$, $a_i$, $b_i$ and $c_0$, $c_j$, $d_j$, where i=1 . . . f, and j=1 . . . h. The first component $F_1(\theta, \phi)$ of the color vector function $F(\theta, \phi)$ is obtained based on the first and second set of coefficients determined in step 114. The results obtained may be converted back to physical values from linearized color space using the reverse of equations (3) and (4).

A numerical example is described below. This example includes four measurements (e=4) at azimuthal angles 32 (θ) of 0°, 90°, 180°, and 270°. Thus f=e/2=2 in equation (2) above. The illumination angle 26 is fixed at 45°. There are six (g=6) aspecular viewing angles φ, −15°, 15°, 25°, 45°, 75°, and 110°. Thus h=3 in equation (3) above. Per step 104 of FIG. 3, the controller 50 is configured to measure the light leaving the measurement location 20 with the plurality of sensors 40A-F at each of the plurality of azimuth angles 32 $(\theta_1, \theta_2 \ldots \theta_e)$ to obtain respective measured color values. Referring to Table 1, a total of 24 sets (4 times 6) of measured L*, a*, b* values are shown.

TABLE 1

| Azimuthal Angle | Aspecular Viewing Angle | L* | a* | b* |
|---|---|---|---|---|
| 0° | −15° | 125.79 | 5.35 | 33.51 |
| 0° | 15° | 116.03 | 5.05 | 30.86 |
| 0° | 25° | 89.98 | 5.2 | 28.2 |
| 0° | 45° | 56.63 | 6.31 | 25.9 |
| 0° | 75° | 40.05 | 8.73 | 27.82 |
| 0° | 110° | 34.63 | 10.91 | 30.38 |
| 90° | −15° | 127.66 | 5.56 | 34.98 |
| 90° | 15° | 116.14 | 6.26 | 32.31 |
| 90° | 25° | 90.76 | 5.87 | 28.87 |
| 90° | 45° | 57.57 | 7.57 | 26.54 |
| 90° | 75° | 40.71 | 8.76 | 28.29 |
| 90° | 110° | 36.09 | 12.28 | 32.06 |
| 180° | −15° | 125.99 | 5.32 | 34.63 |
| 180° | 15° | 115.34 | 5.69 | 32.20 |
| 180° | 25° | 89.87 | 5.13 | 27.56 |
| 180° | 45° | 55.60 | 7.57 | 25.66 |
| 180° | 75° | 40.03 | 7.31 | 27.78 |
| 180° | 110° | 34.86 | 12.21 | 31.97 |
| 270° | −15° | 126.89 | 6.42 | 36.59 |
| 270° | 15° | 116.55 | 7.13 | 32.87 |
| 270° | 25° | 90.97 | 6.03 | 28.33 |
| 270° | 45° | 56.06 | 8.94 | 27.30 |
| 270° | 75° | 40.50 | 8.79 | 28.30 |
| 270° | 110° | 35.50 | 12.97 | 33.48 |

Per step 106 of FIG. 3, the controller 50 is configured to represent the color variation of the surface by a color vector function F(θ, φ) as P(θ).Q(φ). The first component is set to be the lightness L* component. The steps are repeated for the second and third components (a*, b*).

The first function $P_1(\theta)$ for odd values of e may be represented by Eq. (8):

$$a_0/2+a_1\cos(\phi)+b_1\sin(\theta)+\ldots+a_f\cos(f\theta)+b_f\sin(f\theta) \qquad \text{(eq. 8)}$$

The first function $P_1(\theta)$ for even values of e may be represented by Eq. (9):

$$a_0/2+a_1\cos(\theta)+b_1\sin(\theta)+\ldots+a_f/2\cos(f\theta)+b_f\sin(f\theta) \qquad \text{(eq. 9)}$$

In both cases, coefficients $a_x$ and $b_x$ may be estimated from the measured color values using the following equations:

$$a_x = 2/e \sum_{k=0}^{e-1}\left(L_k \cos\frac{2k\pi x}{e}\right) \qquad \text{(eq. 10)}$$

and $$b_x = 2/e \sum_{k=0}^{e-1}\left(L_k \sin\frac{2k\pi x}{e}\right)$$

Note that the term for $a_f$ becomes $a_f/2$ in equation 9 in order to employ the same (eq. 10) for both even and odd values of the total number of azimuth angles (e). The $b_f$ term may be set to zero if the first number (e) is even since:

$$\sin(f \cdot 2k\pi/e) = \sin\frac{e}{2}(2k\pi/e) = \sin k\pi = 0$$

for $k = 0, 1, \ldots, e-1$

In this example, the first function $P_1(\theta)$ is represented as: $P_1=[a_0/2+a_1\cos(\theta)+b_1\sin(\theta)+a_2/2\cos(2\theta)]$. For θ=0, $P_1=(a_0/2+a_1+a_2/2)$. For θ=π/2, $P_1=(a_0/2+b_1-a_2/2)$. For θ=π, $P_1=(a_0/2-a_1+a_2/2)$. For θ=3π/2, $P_1=(a_0/2-b_1-a_2/2)$. Similarly, the second function is represented as: $Q_1(\phi)=[c_0/2+c_1\cos(\phi)+d_1\sin(\phi)\,c_0/2+c_2\cos(2\phi)+d_2\sin(2\phi)+c_3/2.\cos(3\phi)]$.

Per step 108 of FIG. 3, the controller 50 is configured to determine the color vector function $F(\theta, \phi)$ based at least partially on the respective measured color values. Per step 110 of FIG. 4, the non-equally-spaced aspecular viewing angles $\phi$ are converted to equally spaced data points using piecewise linearization equation using equations (4). The converted raw data in radians is shown in Table 2.

TABLE 2

| Azimuthal Angle | Aspecular Viewing Angle | L* | a* | b* |
|---|---|---|---|---|
| 0.00 | −0.26 | 125.79 | 5.35 | 33.51 |
| 0.00 | 0.17 | 117.66 | 5.10 | 31.30 |
| 0.00 | 0.61 | 63.96 | 5.35 | 25.54 |
| 0.00 | 1.05 | 31.64 | 7.14 | 24.18 |
| 0.00 | 1.48 | 34.53 | 9.54 | 28.46 |
| 0.00 | 1.92 | 34.63 | 10.91 | 30.38 |
| 1.57 | −0.26 | 127.66 | 5.56 | 34.98 |
| 1.57 | 0.17 | 118.07 | 6.14 | 32.76 |
| 1.57 | 0.61 | 65.40 | 5.48 | 25.44 |
| 1.57 | 1.05 | 32.70 | 8.84 | 24.79 |
| 1.57 | 1.48 | 35.10 | 9.15 | 28.87 |
| 1.57 | 1.92 | 36.09 | 12.28 | 32.06 |
| 3.14 | −0.26 | 125.99 | 5.32 | 34.63 |
| 3.14 | 0.17 | 117.12 | 5.63 | 32.61 |
| 3.14 | 0.61 | 64.42 | 4.57 | 22.93 |
| 3.14 | 1.05 | 29.92 | 9.39 | 24.23 |
| 3.14 | 1.48 | 34.84 | 7.23 | 28.48 |
| 3.14 | 1.92 | 34.86 | 12.21 | 31.97 |
| 4.71 | −0.26 | 126.89 | 6.42 | 36.59 |
| 4.71 | 0.17 | 118.27 | 7.01 | 33.49 |
| 4.71 | 0.61 | 65.42 | 4.92 | 23.81 |
| 4.71 | 1.05 | 29.90 | 11.13 | 26.52 |
| 4.71 | 1.48 | 35.33 | 8.74 | 28.63 |
| 4.71 | 1.92 | 35.50 | 12.97 | 33.48 |

Per step 112 of FIG. 4, the respective first components $P_1(\theta)$, $Q_1(\phi)$ of the first and second vectors $P(\theta)$, $Q(\phi)$ are expressed as a product of respective plurality of matrices: $P_1(\theta) = A\,p$ and $Q_1(\theta) = q^T B^T$. Here $p = [a_0/2, a_1, b_1, a_2/2]$, a 4×1 vector, and A is the 4×4 matrix:

$$\begin{bmatrix} 1 & 1 & 0 & 1 \\ 1 & 0 & 1 & -1 \\ 1 & -1 & 0 & 1 \\ 1 & 0 & -1 & -1 \end{bmatrix}$$

The matrix $q = [c_0/2, c_1, d_1, c_2, d_2, c_3/2]^T$ is a 6×1 vector, and B is the 6×6 matrix:

$$\begin{bmatrix} 1 & 1 & 0 & 1 & 0 & 1 \\ 1 & .5 & .866 & -.5 & .866 & -1 \\ 1 & -.5 & .866 & -.5 & -.866 & 1 \\ 1 & -1 & 0 & 1 & 0 & -1 \\ 1 & -.5 & -.866 & -.5 & .866 & 1 \\ 1 & .5 & -.866 & -.5 & -.866 & -1 \end{bmatrix}$$

Per step 114 of FIG. 4, controller 50 is configured to input the measured color values (matrix $F_1$) into the respective plurality of matrices to obtain the first and second set of coefficients. Here $F_1$ is the 4×6 matrix with its 24 elements taken from the L* values shown in Table 2. Matrix $F_1$ is inputted into equation (7), $p\,q^T = A^{-1} F_1 B^{-T}$. In this case, $p\,q^T$ becomes:

$$\begin{bmatrix} 68.4 & 40.7 & 32.4 & 10.4 & 15.2 & 7.0 \\ .088 & -.230 & .089 & .292 & .133 & -.250 \\ .309 & -.285 & -.084 & -.144 & -.144 & -.223 \\ -.457 & -.151 & -.061 & -.019 & .139 & -.065 \end{bmatrix}$$

The first component $F_1(\theta, \phi)$ of the color vector function $F(\theta, \phi)$ may now be expressed as:

$$[1 \; \cos\theta \; \sin\theta \; \cos 2\theta] * \begin{bmatrix} 68.4 & 40.7 & 32.4 & 10.4 & 15.2 & 7.0 \\ .088 & -.230 & .089 & .292 & .133 & -.250 \\ .309 & -.285 & -.084 & -.144 & -.144 & -.223 \\ -.457 & -.151 & -.061 & -.019 & .139 & -.065 \end{bmatrix} \begin{bmatrix} 1 \\ \cos\varphi \\ \sin\varphi \\ \cos 2\varphi \\ \sin 2\varphi \\ \cos 3\varphi \end{bmatrix}$$

The first component $F_1(\theta, \phi)$ allows the calculation of the first component (L* in this case, repeated in a similar fashion for a* or b*) values for any azimuth or viewing angle $(\theta, \phi)$.

The controller 50 of FIG. 1 may be configured to employ any of a number of computer operating systems and generally include computer-executable instructions, where the instructions may be executable by one or more computers. Computer-executable instructions may be compiled or interpreted from computer programs created using a variety of well-known programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of known computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

The invention claimed is:

1. A system of characterizing a color variation of a surface, the system comprising:
   a device having a light source configured to direct a beam of light on a measurement location on the surface, the light source being at an illumination angle relative to the measurement location;
   wherein the device is rotatable to a plurality of azimuth angles ($\theta_1, \theta_2 \ldots \theta_e$), relative to the measurement location, a total number of the plurality of azimuth angles being at least a first number (e);
   wherein the device includes a plurality of sensors positioned at respective viewing angles ($\phi_1, \phi_2 \ldots \phi_g$), a total number of the respective viewing angles being at least a second number (g);
   a controller operatively connected to the device; and
   an algorithm stored on and executable by the controller to cause the controller to:
     direct a beam of light at the measurement location through the light source;
     measure the light leaving the measurement location with the plurality of sensors at each of the plurality of azimuth angles ($\theta_1, \theta_2 \ldots \theta_e$) to obtain respective measured color values;
     define a color vector function $F(\theta, \phi)$ as a product of a first vector $P(\theta)$ dependent on the plurality of azimuth angles and a second vector $Q(\phi)$ dependent on the respective viewing angles such that $F(\theta, \phi)=P(\theta) \cdot Q(\phi)$, the color vector function $F(\theta, \phi)$ representing the color variation of the surface; and
     determine the color vector function $F(\theta, \phi)$ based at least partially on the respective measured color values.

2. The system of claim 1, wherein the device is a spectrophotometer.

3. The system of claim 1, wherein the plurality of azimuth angles ($\theta_1, \theta_2 \ldots \theta_e$) are evenly spaced.

4. The system of claim 1, wherein the illumination angle is approximately 45 degrees.

5. The system of claim 1, wherein:
   the color vector function $F(\theta, \phi)$ and first and second vectors $P(\theta), Q(\phi)$ each include respective first, second and third components, such that $F(\theta, \phi)=[F_1(\theta, \phi), F_2(\theta, \phi), F_3(\theta, \phi)]$, $P(\theta)=[P_1(\theta), P_2(\theta), P_3(\theta)]$ and $Q(\phi)=[Q_1(\phi), Q_2(\phi), Q_3(\phi)]$.

6. The system of claim 5, wherein the respective first component of the color vector function $F(\theta, \phi)$ represents one of:
   a lightness component (L*), a redness/greenness component (a*) and a yellowness/blueness component (b*).

7. The system of claim 5, wherein execution of the algorithm to determine the color vector function $F(\theta, \phi)$ based at least partially on the measured color values causes the controller to:
   express the respective first components $P_1(\theta), Q_1(\phi)$ of the first and second vectors $P(\theta), Q(\phi)$ as a product of respective plurality of matrices;
   obtain a first and second set of coefficients by inputting the measured color values into the respective plurality of matrices; and
   obtain the respective first component $F_1(\theta, \phi)$ of the color vector function $F(\theta, \phi)$ based on the first and second set of coefficients.

8. The system of claim 5, wherein execution of the algorithm to define the color vector function $F(\theta, \phi)$ causes the controller to:
   define an integer parameter f such that $f=e/2$ and $f=(e-1)/2$ if the first number (e) is even and odd, respectively;
   represent the respective first component $P_1(\theta)$ of the first vector $P(\theta)$ as: $P_1(\theta)=a_0/2+\Sigma_{j=1 \, to \, f}[a_j \cos(j\theta)+b_j \sin(j\theta)]$;
   wherein a first set of coefficients include $a_0, a_j, b_j$ ($j=1 \ldots f$); and
   $b_{j=f}$ is zero if the first number (e) is even.

9. The system of claim 5, wherein execution of the algorithm to define the color vector function $F(\theta, \phi)$ causes the controller to:
   define an integer parameter h such that $h=g/2$ and $h=(g-1)/2$ if the second number (g) is even and odd, respectively;
   represent the respective first component $Q_1(\phi)$ of the second vector $Q(\phi)$ as: $Q_1(\phi)=c_0/2+\Sigma_{k=1 \, to \, h}[c_k \cos(k\phi)+d_k \sin(k\phi)]$;
   wherein a second set of coefficients include $c_0, c_k, d_k$ ($k=1 \ldots h$); and
   $d_{k=h}$ is zero if the second number (g) is even.

10. A method of characterizing a color variation of a surface, the method comprising:
    positioning a device having a light source placed at an illumination angle relative to a measurement location on the surface;
    wherein the device is rotatable to a plurality of azimuth angles ($\theta_1, \theta_2 \ldots \theta_e$), relative to the measurement location, a total number of the plurality of azimuth angles being at least a first number (e);
    positioning a plurality of sensors in the device at respective viewing angles ($\phi_1, \phi_2 \ldots \phi_g$), a total number of the respective viewing angles being at least a second number (g);
    directing a beam of light at the measurement location with the light source;

measuring the light leaving the measurement location with the plurality of sensors at each of the plurality of azimuth angles ($\theta_1, \theta_2 \ldots \theta_e$) to obtain respective measured color values;

defining a color vector function $F(\theta, \phi)$ as a product of a first vector $P(\theta)$ dependent on the plurality of azimuth angles and a second vector $Q(\phi)$ dependent on the respective viewing angles such that $F(\theta, \phi) = P(\theta) \cdot Q(\phi)$, the color vector function $F(\theta, \phi)$ representing the color variation of the surface; and determining the color vector function $F(\theta, \phi)$ based at least partially on the respective measured color values.

11. The method of claim 10, wherein each of the respective measured color values include a lightness component (L*), a redness/greenness component (a*) and yellowness/blueness component (b*).

12. The method of claim 10, wherein:

the color vector function $F(\theta, \phi)$ and first and second vectors $P(\theta), Q(\phi)$ each include respective first, second and third components, such that $F(\theta, \phi) = [F_1(\theta, \phi), F_2(\theta, \phi), F_3(\theta, \phi)]$, $P(\theta) = [P_1(\theta), P_2(\theta), P_3(\theta)]$ and $Q(\phi) = [Q_1(\phi), Q_2(\phi), Q_3(\phi)]$.

13. The method of claim 12, wherein the respective first component of the color vector function $F(\theta, \phi)$ represents one of:

a lightness component (L*), a redness/greenness component (a*) and a yellowness/blueness component (b*).

14. The method of claim 12, wherein the determination of the color vector function $F(\theta, \phi)$ based at least partially on the measured color values includes:

expressing the respective first components of the first and second vectors $P(\theta), Q(\phi)$ as a product of respective plurality of matrices;

obtaining a first and a second set of coefficients by inputting the measured color values into the respective plurality of matrices; and obtaining the respective first component $F_1(\theta, \phi)$ of the color vector function $F(\theta, \phi)$ based on the first and second set of coefficients.

15. The method of claim 12, wherein defining the color vector function $F(\theta, \phi)$ includes:

representing the respective first component $P_1(\theta)$ of the first vector $P(\theta)$ as a first function dependent on a first set of coefficients; and representing the respective first component $Q_1(\phi)$ of the second vector as a second function dependent on a second set of coefficients.

16. The method of claim 12, wherein:

the first function is $P_1(\theta) = a_0/2 + \Sigma_{j+1\ to\ f}[a_j \cos(j\theta) + b_j \sin(j\theta)]$;

f is an integer parameter such that $f = e/2$ and $f = (e-1)/2$ if the first number (e) is even and odd, respectively;

the first set of coefficients include $a_0, a_j, b_j$ ($j = 1 \ldots f$); and $b_{j=f}$ is zero if the first number (e) is even.

17. The method of claim 12, wherein:

the second function is $Q_1(\phi) = c_0/2 + \Sigma_{k\ =to\ h}[c_k \cos(k\phi) + d_k \sin(k\phi)]$;

h is an integer parameter such that $h = g/2$ and $h = (g-1)/2$ if the second number (g) is even and odd, respectively;

the second set of coefficients include $c_0, c_k, d_k$ ($k = 1 \ldots h$); and $d_{k=h}$ is zero if the second number (g) is even.

* * * * *